United States Patent
Ortigosa et al.

(10) Patent No.: US 9,822,158 B2
(45) Date of Patent: Nov. 21, 2017

(54) METHOD FOR PREPARING CRYSTALLINE INSULIN

(71) Applicant: Merck Sharp & Dohme Corp., Rahway, NJ (US)

(72) Inventors: Allison D. Ortigosa, Harrisonburg, VA (US); William Perry, Longmont, CO (US); Mark C. Sleevi, Longmont, CO (US); Luis Sierra, Dunellen, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/038,495

(22) PCT Filed: Dec. 1, 2014

(86) PCT No.: PCT/US2014/067847
§ 371 (c)(1),
(2) Date: May 23, 2016

(87) PCT Pub. No.: WO2015/084694
PCT Pub. Date: Jun. 11, 2015

(65) Prior Publication Data
US 2016/0297862 A1    Oct. 13, 2016

Related U.S. Application Data

(60) Provisional application No. 61/911,514, filed on Dec. 4, 2013.

(51) Int. Cl.
*C07K 1/30* (2006.01)
*C07K 14/62* (2006.01)
*C07K 1/113* (2006.01)

(52) U.S. Cl.
CPC ............ *C07K 14/62* (2013.01); *C07K 1/1136* (2013.01); *C07K 1/306* (2013.01); *C07B 2200/13* (2013.01)

(58) Field of Classification Search
CPC ...... C07K 1/306; C07K 14/62; C07K 14/622; C07K 14/625
See application file for complete search history.

(56) References Cited

U.S. PATENT DOCUMENTS

| | | | | |
|---|---|---|---|---|
| 4,476,118 A | * | 10/1984 | Brange | H05K 13/06 514/6.4 |
| 5,157,021 A | * | 10/1992 | Balschmidt | C07K 14/62 514/5.9 |
| 5,981,751 A | | 11/1999 | Mudryk et al. | |
| 6,818,738 B2 | * | 11/2004 | Havelund | A61K 9/0075 530/303 |
| 7,875,700 B2 | | 1/2011 | Radhakrishnan et al. | |
| 9,187,520 B2 | * | 11/2015 | Wang | C07K 14/62 |

FOREIGN PATENT DOCUMENTS

| | | |
|---|---|---|
| CN | 102219851 | 5/2012 |
| WO | 2008065138 | 6/2008 |

OTHER PUBLICATIONS

Jackson et al., Preparation an Partial Characterization of Crystalline Human Insulin, (1969), Diabetes, pp. 206-211, vol. 18, Iss. 4.
Sutherland, Fine Chemical Filtration: Defining Filtration Process, Filtration+Separation, (2007),pp. 38-39, BNSDOCID: <XP 22023371A_i_>.

* cited by examiner

*Primary Examiner* — Jeffrey E Russel
(74) *Attorney, Agent, or Firm* — John David Reilly; Gloria Fuentes

(57) ABSTRACT

A method for crystallizing insulin or insulin analogs under alkaline conditions and purifying the insulin or insulin analog crystals by filtering through a filter and drying the insulin or insulin analog crystals captured on the filter to produce crystalline insulin or insulin analog crystal compositions is described. In particular aspects, the method may be used to crystalize insulin glargine.

19 Claims, 2 Drawing Sheets

METHOD FOR PREPARING CRYSTALLINE INSULIN

CROSS REFERENCE TO RELATED APPLICATIONS

This application is the National Stage of International Application No. PCT/US2014/067847 filed on Dec. 1, 2014, which claims the benefit under 35 U.S.C. 119(e) of U.S. Provisional Application No. 61/911,514, filed Dec. 4, 2013.

REFERENCE TO SEQUENCE LISTING SUBMITTED ELECTRONICALLY

The sequence listing of the present application is submitted electronically via EFS-Web as an ASCII formatted sequence listing with a file name "23636WOPCTSEQ.txt", creation date of 23 May 2016, and a size of 1 KB. This sequence listing submitted via EFS-Web is part of the specification and is herein incorporated by reference in its entirety.

BACKGROUND OF THE INVENTION (1) Field of the Invention

The present invention relates to a method for crystallizing insulin or insulin analogs under alkaline conditions and purifying the insulin or insulin analog crystals by filtering through a filter and drying the insulin or insulin analog crystals captured on the filter to produce crystalline insulin or insulin analog crystal compositions. In particular aspects, the present invention relates to a method for preparing crystals of insulin glargine.

(2) Description of Related Art

Diabetes mellitus is a chronic metabolic disorder caused by either a deficiency of insulin generated by pancreatic beta cells (Type 1) or an acquired cellular resistance to insulin (Type 2). Both Type 1 and Type 2 diabetes result in hyperglycemia, which can in turn result in long term complications. Since the introduction of insulin in 1921, all forms of diabetes have become treatable.

It is well known in the art that insulin may be crystallized in the presence of zinc ions, resulting in a crystalline preparation with significant benefits over amorphous, uncrystallized insulin with regards to stability, storage, formulation, and/or administration. Methods for crystallizing insulin or insulin analogs have been disclosed in U.S. Pat. Nos. 5,952,297; 5,028,587; 5,504,188; 5,952,297 and 7,193,035. Methods for crystallizing an insulin analog in the absence of zinc ions is disclosed in U.S. Pat. No. 7,193,035, which discloses zinc-free crystallization of an insulin analog performed at a pH in the range of about 4.0 to about 7.5. Methods for crystallizing mixed crystals of insulin and insulin derivatives is disclosed in U.S. Pat. No. 5,028,587. Mühlig et al., J. Crystal Growth 232: 93-101 (2001) describe a modified batch crystallization method that was used to prepare crystals of insulin glargine.

While there are methods available for crystallizing insulin and insulin analogs, there is a need in the art for alternative methods of crystallizing insulin or insulin analogs.

BRIEF SUMMARY OF THE INVENTION

The present invention provides a method for crystallizing insulin or insulin analogs under alkaline conditions. In an effort to provide improved methods for preparing crystalline insulin or insulin analogs, we have found that insulin or insulin analogs may be crystallized at a pH that is at least one or more pH units greater than the isoelectric point (pI) of the insulin or insulin analog. Current methods for preparing insulin crystals are usually performed at a pH slightly above or less than the pI of the insulin. The present invention enables the production of large, ordered crystals of the insulin or insulin analog that may be about 10 μm or greater in size and which are amenable to purifying by collecting the crystals in a filter apparatus and drying the crystals in the same filtering apparatus to produce crystalline insulin compositions.

Therefore, the present invention provides a method for preparing insulin or insulin analog crystals which comprises crystallizing the insulin or insulin analog from an aqueous solution comprising the insulin or the insulin analog, a water miscible organic solvent, a crystal stabilizing agent, zinc salt, wherein the solution has a pH greater than the pI of the insulin or insulin analog. In particular aspects, the insulin or insulin analog may be crystallized at a pH that is at least 1.0 or more pH units greater than the isoelectric point (pI) of the insulin or insulin analog. In particular aspects, the insulin or insulin analog may be crystallized at a pH that is at least 1.5 or more pH units greater than the isoelectric point (pI) of the insulin or insulin analog. In particular aspects, the insulin or insulin analog may be crystallized at a pH that is at least 2.0 or more pH units greater than the isoelectric point (pI) of the insulin or insulin analog. In particular aspects, the insulin or insulin analog may be crystallized at a pH that is at least 2.5 or more pH units greater than the isoelectric point (pI) of the insulin or insulin analog. In particular aspects, the insulin or insulin analog may be crystallized at a pH that is between about 1.0 and 3.5 pH units greater than the isoelectric point (pI) of the insulin or insulin analog. In particular aspects, the insulin or insulin analog may be crystallized at a pH that is between about 1.5 and 3.5 pH units greater than the isoelectric point (pI) of the insulin or insulin analog. In particular aspects, the insulin or insulin analog may be crystallized at a pH that is between about 2.0 and 3.5 pH units greater than the isoelectric point (pI) of the insulin or insulin analog. In particular aspects, the method may be performed at a temperature at room temperature or within the range of about 17° C. to 23° C., or about 20° C., and at a pH within the range of about 8.0 to 9.5 pH units or about 9.1 to 9.3 pH units, or about 9.2 pH units. In further aspects, the solution is incubated with agitation or stirring. The agitation may be provided by a low shear impeller, for example, an axial flow impeller such as marine impeller or pitched-blade impeller.

In a further aspect of the method, the solution comprises ammonium acetate, which may in particular aspects comprise ammonium acetate at a concentration of about 50 mM to 150 mM. In further embodiments, the ammonium acetate concentration is about 80 mM to 100 mM. In further embodiments, the ammonium acetate concentration is about 80 mM to 90 mM. In particular aspects, the ammonium acetate concentration about 85 mM.

In a further aspect of the method, the concentration of the insulin or insulin analog in the solution may be about 1 to about 13 grams of insulin or insulin analog per liter of solution. In a further aspect, the concentration of the insulin or insulin analog in the solution may be about 1 to about 13 grams of insulin or insulin analog per liter of solution. In a further aspect, the concentration of the insulin or insulin analog in the solution may be about 1 to about 10 grams of insulin or insulin analog per liter of solution. In a further aspect, the concentration of the insulin or insulin analog in the solution may be about 1 to about 5 grams of insulin or insulin analog per liter of solution. In a further aspect, the concentration of the insulin or insulin analog in the solution may be about 1 to about 4 grams of insulin or insulin analog per liter of solution. In a further aspect, the concentration of the insulin or insulin analog in the solution may be about 1 to about 3 grams of insulin or insulin analog per liter of solution. In a further aspect, the concentration of the insulin or insulin analog in the solution may be about 1.75 to about 2.25 grams of insulin or insulin analog per liter of solution. In a particular aspect, the concentration of the insulin or insulin analog in the crystallization solution may be about 2 grams per liter.

In a further aspect of the method, the solution may comprise from about 0% (v/v) to about 20% (v/v) of the water miscible organic co-solvent. In a further aspect of the method, the solution comprises from about 5% (v/v) to about 20% (v/v) of the water miscible organic co-solvent. In a further aspect, the solution comprises from about 9% (v/v) to about 11% (v/v) of the water miscible organic solvent. In a further aspect, the solution comprises from about 9.5% (v/v) to about 10.5% (v/v) of the water miscible organic solvent. In a further aspect, the solution comprises about 10% (v/v) of the water miscible organic solvent. In particular aspects, the water miscible organic solvent is isopropanol.

In particular aspects, the solution comprises from about 0.10% (v/v) to about 0.30% (v/v) of the crystal stabilizing agent. In particular aspects, the solution comprises from about 0.15% (v/v) to about 0.25% (v/v) or 0.20% (v/v) of the crystal stabilizing agent. In a further aspect of the method, the crystal stabilizing agent is a phenolic agent. In a further aspect of the method, the crystal stabilizing agent is selected from the group comprising resorcinol, cresol, meta-cresol, phenol, methyl p-hydroxybenzoate, and methyl 4-hydroxybenzoate. In a particular aspect, the crystal stabilizing agent is meta-cresol.

In a further aspect of the method, the amount of zinc salt in the solution is an amount sufficient to provide at least two molecules of zinc per six molecules of insulin or insulin analog. In particular aspects, the amount of zinc salt in the solution is an amount sufficient to provide at least four molecules of zinc per six molecules of insulin or insulin analog. In particular aspects, the amount of zinc salt in the solution is an amount sufficient to provide about two to about four molecules of zinc per six molecules of insulin or insulin analog. In particular aspects the zinc salt is zinc chloride and the zinc chloride is at a concentration of about 13 mg to 17 mg per gram of insulin or insulin analog. In a particular aspect, the amount of zinc chloride in the solution is 15 mg or about 15 mg per gram of insulin or insulin analog.

In particular aspects of the method, the insulin is native human, porcine, or bovine insulin. In further aspects, the insulin analog is an acid-stable insulin analog, which is stable and soluble in acidic or weakly acidic solutions and insoluble or partially insoluble at physiological pH, or a pI-shifted insulin analog in which the pI of the insulin analog is less than or greater than the pI of native human insulin. The pI of native insulin is 5.4 to 5.6, thus the pI-shifted insulin analog has a pI less than 5.4 or greater than 5.6. In particular aspects the insulin analog has a pI from between 5.8 to 8.0. An acid-stable insulin analog such as insulin glargine has a pI of about 6.7 to 7.4. In a further aspect, the insulin analog is insulin glargine.

The present invention further provides a method for preparing insulin glargine crystals which comprises crystallizing the insulin glargine from an aqueous solution comprising the insulin glargine, a water miscible organic solvent, a crystal stabilizing agent, zinc salt, wherein the solution has a pH at least 1, 1.5, 2, or 3 pH units greater than the pI of the insulin glargine. In particular aspects, the method may be performed at a temperature at room temperature or within the range of 17° C. to 23° C., or about 20° C., and at a pH within the range of 9.1 to 9.3 pH units, or about 9.2 pH units. In further aspects, the solution is incubated with agitation or stirring. The agitation may be provided by a low shear impeller, for example, an axial flow impeller such as marine impeller or pitched-blade impeller.

In a further aspect of the method, the solution comprises ammonium acetate, which may in particular aspects comprise ammonium acetate at a concentration of about 80 mM to about 150 mM. In a further aspect of the method, the solution comprises ammonium acetate, which may in particular aspects comprise ammonium acetate at a concentration of about 80 mM to about 100 mM. In a further aspect of the method, the solution comprises ammonium acetate, which may in particular aspects comprise ammonium acetate at a concentration of about 80 mM to about 90 mM. In further aspects, the concentration of the ammonium acetate in the solution may be 85 mM or about 85 mM.

In a further aspect of the method, the concentration of the insulin glargine in the solution may be about 1 to 3, 4, 5, 10, 15, or 20 grams of insulin or insulin analog per liter of solution. In a further aspect, the concentration of the insulin glargine in the solution may be about 1.75 to about 2.25 grams of insulin glargine per liter of solution. In a particular aspect, the concentration of the insulin glargine in the crystallization solution may be about 2 grams per liter.

In a further aspect of the method, the solution comprises from about 0% (v/v) to about 20% (v/v) of the water miscible organic co-solvent. In a further aspect of the method, the solution comprises from about 5% (v/v) to about 20% (v/v) of the water miscible organic co-solvent. In a further aspect, the solution comprises from about 9% (v/v) to about 11% (v/v) of the water miscible organic solvent. In a further aspect, the solution comprises from about 9.5% (v/v) to about 10.5% (v/v) of the water miscible organic solvent. In a further aspect, the solution comprises about 10% (v/v) of the water miscible organic solvent. In particular aspects, the water miscible organic solvent is isopropanol.

In particular aspects, the solution comprises from about 0.10% (v/v) to about 0.30% (v/v) of the crystal stabilizing agent. In particular aspects, the solution comprises from about 0.15% (v/v) to about 0.25% (v/v) or 0.20% (v/v) of the crystal stabilizing agent. In a further aspect of the method, the crystal stabilizing agent is a phenolic agent. In a further aspect of the method, the crystal stabilizing agent is selected from the group comprising resorcinol, cresol, meta-cresol, phenol, methyl p-hydroxybenzoate, and methyl 4-hydroxybenzoate. In a particular aspect, the crystal stabilizing agent is meta-cresol.

In a further aspect of the method, the amount of zinc salt in the solution is an amount that provides at least two molecules of zinc per six molecules of insulin or insulin analog. In a further aspect of the method, the amount of zinc salt in the solution is an amount that provides at least four molecules of zinc per six molecules of insulin or insulin analog. In a further aspect of the method, the amount of zinc salt in the solution is an amount that provides about two molecules to about four molecules of zinc per six molecules of insulin or insulin analog. In particular aspects, the zinc salt is zinc chloride and is amount of about 13 mg to about 17 mg per gram of insulin glargine. In a particular aspect, the amount of zinc chloride in the solution is 15 mg or about 15 mg per gram of insulin glargine.

DEFINITIONS

As used herein, the term "insulin" means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus.

The term "insulin" or "insulin molecule" is a generic term that designates the 51 amino acid heterodimer comprising the A-chain peptide having the amino acid sequence shown in SEQ ID NO: 1 and the B-chain peptide having the amino acid sequence shown in SEQ ID NO: 2, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

The term "insulin analog" as used herein includes any heterodimer analog that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; and/or deleting any or all of positions B1-4 and B26-30. Insulin analogues include molecules having one to 10 amino acids at the N or C terminus of the A-chain peptide and/or B-chain peptide. Insulin analogs further include molecules amidated at the C-terminus of the A-chain peptide and/or B-chain peptide. Examples of insulin analogs include but are not limited to the heterodimer analogs disclosed in published international application WO20100080606, WO2009/099763, and WO2010080609, the disclosures of which are incorporated herein by reference. Insulin glargine (Gly(A21), Arg(B31), Arg(B32)-human insulin is an example of a commercially available insulin analog.

The term "insulin analogs" further includes heterodimer polypeptide molecules that have little or no detectable activity at the insulin receptor but which have been modified to include one or more amino acid modifications or substitutions to have an activity at the insulin receptor that has at least 1%, 10%, 50%, 75%, or 90% of the activity at the insulin receptor as compared to native insulin. In particular aspects, the insulin analog is a partial agonist that has from 2× to 100× less activity at the insulin receptor as does native insulin. In other aspects, the insulin analog has enhanced activity at the insulin receptor.

DETAILED DESCRIPTION OF THE INVENTION

Figure 1A:
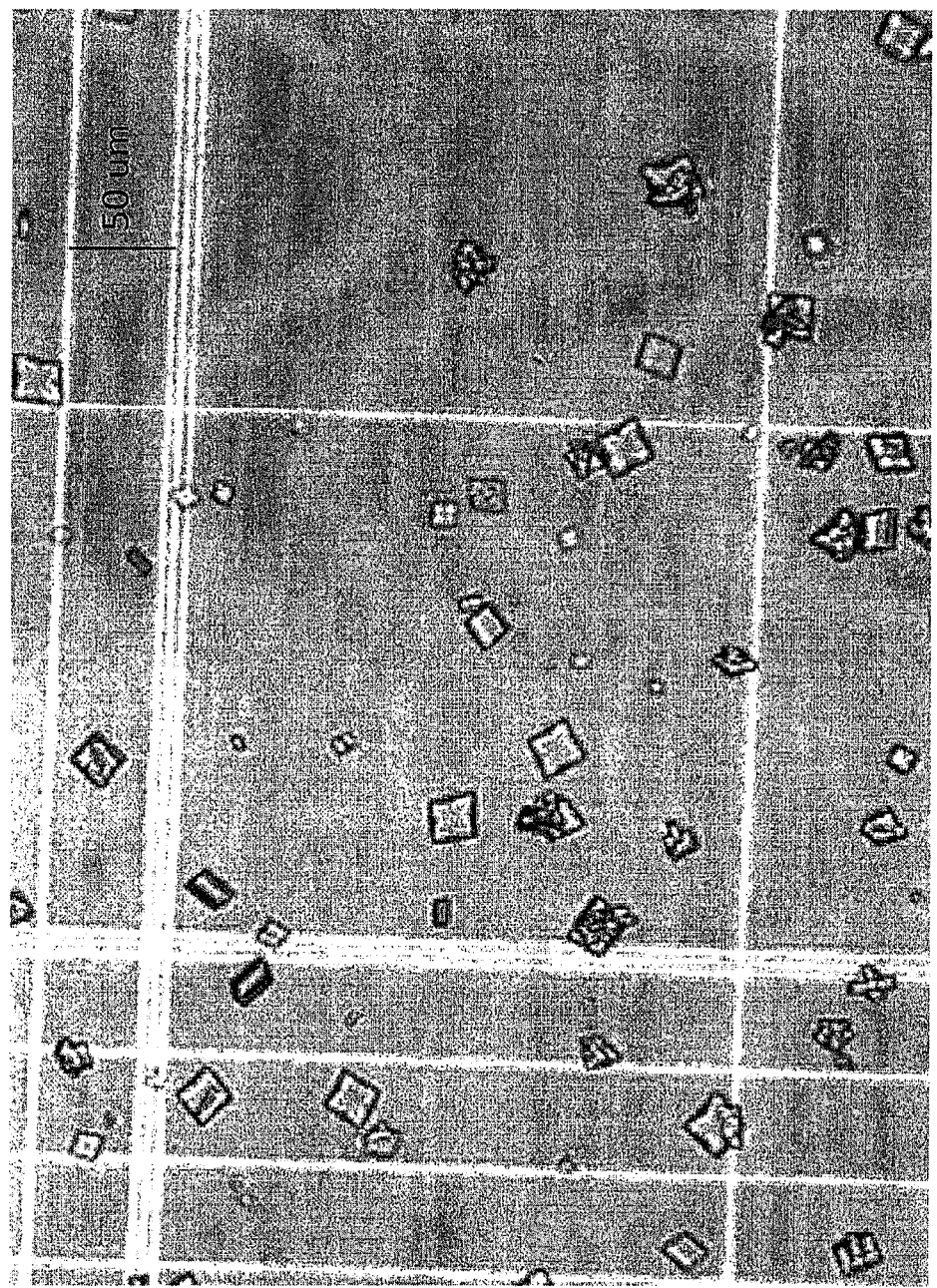
FIG. 1A shows a photomicrograph of insulin glargine crystals produced by the method disclosed herein.

The present invention provides a method for crystallizing insulin or insulin analogs under alkaline conditions. Current methods for preparing insulin crystals are usually performed at a pH slightly above or less than the isoelectric point (pI) of the insulin. However, we have found that insulin or insulin analogs may be crystallized at an alkaline pH that is at least one or more pH units greater than the pI of the insulin or insulin analog and when they are crystallized using the method herein, large, ordered crystals of the insulin or insulin analog are produced. These large insulin crystals may be recovered from the crystallization solution by filtration through a filter apparatus and then dried in the filter apparatus. In many current methods for producing insulin crystals, the crystals produced may be too small to be efficiently separated from the crystallization solution by filtration. Therefore, in many current methods, the insulin crystals are separated from the crystalizing solution by centrifugation. The method disclosed herein is capable of producing a preparation of insulin or insulin analog zinc hexamers with purity greater than about 99% and a yield of about 90% to 100% recovery of the insulin or insulin analog.

An important aspect of the method disclosed here is that it enables the production of large insulin or insulin analog crystals that are about 10 μm or greater in size in high yield. The inventors have discovered that inducing crystallization of insulin or insulin analog in a solution at a pH that is greater than the pI of the insulin or insulin analog molecule facilitates the formation of insulin or insulin analog crystals that are able to be separated from the crystallization solution by filtering through a filter apparatus and then dried in the same filter apparatus. An example of a filter apparatus suitable for filtering and drying the insulin or insulin analog crystals is an agitated Nutsche filter apparatus. It was further found that by including a water miscible organic solvent (for example, isopropanol) in the crystallization solution, an enhanced rate of crystallization of the insulin or insulin analog and the formation of the large insulin or insulin analog crystals occurred.

In general, insulin or insulin analog in about 80 to 150 mM ammonium acetate buffer is introduced into a crystallization vessel. To the insulin or insulin analog solution, 80 to 150 mM ammonium acetate buffer, optionally a water miscible organic solvent, a crystal stabilizing agent, and zinc salt solution are added in the correct ratios to target an insulin or insulin analog concentration of about 1 to 13 g/L for crystallization and the solution is mixed with a low shear marine impeller.

An important aspect of the invention is that the solution of insulin or insulin analog is prepared and the pH adjusted to a pH at least 1, 1.5, 2, or 3 pH units greater than the pI of the insulin or insulin analog before the zinc salt is added to the solution to provide a crystallizing solution that induces crystallization of the insulin or insulin analog therein. The order the water miscible organic solvent and the crystal stabilizing agent are added to the insulin or insulin analog solution may be varied provided the pH of the solution is adjusted prior to the addition of the zinc salt. Thus, an aqueous solution of insulin or insulin analog is provided comprising or consisting essentially of about ammonium acetate, a water miscible organic solvent, and a crystal stabilizing agent. The concentration of the insulin or insulin analog is about 1 to 13, 1 to 10, 1 to 5, 1 to 4, 1 to 3, 1.75 to 2.25 g/L or about 2.0 g/L of insulin or insulin analog per liter of crystallizing solution. The ammonium acetate may be about 80 to 150 mM or about 80 to 100 mM or about 80 mM to 90 mM or about 85 mM. The water miscible organic solvent may be at a concentration of about 0% to 20% (v/v) or 5% to 20% (v/v) or about 9.5 to 11% (v/v) or about 10% (v/v). Representative examples of water miscible organic solvents include ethanol, methanol, acetone, glycerol, and isopropanol. In particular aspects, the water miscible organic solvent is isopropanol. The crystal stabilizing agent may be at a concentration of about 0.15% to 0.25% (w/v) or about 0.2% (w/v) to improve stability. The crystal stabilizing agent interacts with the insulin or insulin analog when the pH of the aqueous solution is adjusted to a pH that is greater than the pI of the insulin or insulin analog. Representative examples of crystal stabilizing agents include phenolic agents such as resorcinol, cresol, meta-cresol, phenol, methyl p-hydroxybenzoate, and methyl 4-hydroxybenzoate. In particular aspects, the crystal stabilizing agent is meta-cresol. The pH of the aqueous solution is adjusted to be at a pH that is at least 1, 2, 2.5, or 3 pH units greater than the pI of the insulin or insulin analog using a base such as ammonium hydroxide. In particular aspects the pH is adjusted to about 9.1 to 9.3 or 9.2 using a base such as 50% ammonium hydroxide. By way of example, the pI of native insulin is 5.4 to 5.6 whereas an acid-stable insulin analog such as insulin glargine has a pI of about 6.7 to 7.4. The crystal stabilizing agent interacts with the insulin or insulin analog at a pH that is greater than the pI of the insulin or insulin analog.

To initiate crystal formation, a defined amount of a zinc salt stock solution is added to the above solution in an amount sufficient to provide a crystallizing solution comprising at least two to four zinc molecules per six molecules of insulin or insulin analog. In particular aspects, the crystallizing solution comprises about 1.5 moles of insulin for every mole of zinc salt. Insulin or insulin analog will form a hexamer with two zinc molecules; this is the primary building component of crystals. Representative examples of zinc salts include zinc acetate, zinc bromide, zinc chloride, zinc fluoride, zinc iodide and zinc sulfate. As an example, when the Zinc salt is zinc chloride, the final zinc chloride concentration is about 14.7 mg to about 15.3 mg of zinc chloride to every gram of the insulin to initiate crystal formation. The slurry is allowed to mix and incubate for a defined time to further promote crystal formation.

In another embodiment of the invention, crystallization comprises the following steps. First, 100 mM ammonium acetate solution at a pH below the pI of the insulin or insulin analog (for example, about 2.9 to 3.3 pH units or 3.1 pH units) is added to the insulin or insulin analog solution in the vessel.

Second, a water miscible organic solvent as described above may be added to the solution in an amount that will provide a final water miscible organic solvent concentration of about 5% (v/v) to 20% (/v/) or 9.5 to 11% (v/v) or 10% (v/v) and/or the solution is then pH adjusted up to a pH that is at least 1, 2, 2.5, or 3 pH units greater than the pI of the insulin or insulin analog using a base such as ammonium hydroxide. In particular aspects the pH is adjusted to about 9.1 to 9.3 or 9.2 using a base such as 50% ammonium hydroxide.

Third, a crystal stabilizing agent as described above is then added to the solution in an amount that will provide a final concentration of about 0.15% to 0.25% (w/v) or about 0.2% (w/v) to improve stability. The crystal stabilizing agent interacts with the insulin or insulin analog at a pH that is greater than the pI of the insulin or insulin analog.

Finally, a defined amount of a zinc salt as described above is added to the solution to provide a crystallizing solution comprising at least two to four zinc molecules per six molecules of insulin or insulin analog to initiate crystal formation. Representative examples of zinc salts include zinc acetate, zinc bromide, zinc chloride, zinc fluoride, zinc iodide and zinc sulfate. As an example, when the Zinc salt is zinc chloride, the final zinc chloride concentration is about 1.47 grams to about 1.53 grams of zinc chloride to every gram of the insulin to initiate crystal formation. The slurry is allowed to mix and incubate for a defined time to further promote crystal formation.

In a further embodiment of the invention, crystallization comprises the following steps. First, 100 mM ammonium acetate solution at a pH below the pI of the insulin or insulin analog (for example, about 2.9 to 3.3 pH units or 3.1 pH units) is added to the insulin or insulin analog solution in the vessel.

Second, a water miscible organic solvent as described above may be added to the solution in an amount that will provide a final water miscible organic solvent concentration of about 5% to 20% (v/v) or 9.5 to 11% (v/v) or 10% (v/v). This step is optional.

Third, a crystal stabilizing agent as described above is then added to the solution in an amount that will provide a final concentration of about 0.15% to 0.25% (w/v) or about 0.2% (w/v) to improve stability. This solution is pH adjusted up to a pH that is at least 1, 2, 2.5, or 3 pH units greater than the pI of the insulin or insulin analog using a base such as ammonium hydroxide. In particular aspects the pH is adjusted to about 9.1 to 9.3 or 9.2 using a base such as 50% ammonium hydroxide.

Finally, a defined amount of a zinc salt as described above is added to the solution to provide a crystallizing solution comprising at least two to four zinc molecules per six molecules of insulin or insulin analog to initiate crystal formation. The slurry is allowed to mix and incubate for a defined time to further promote crystal formation.

In any one of the above embodiments, crystallization is usually complete in about 5 to 8 hours. During crystallization, a low shear, axial flow impeller (e.g., pitched-blade or marine impeller) is used to provide just enough mixing power input to circulate the solution. After crystallization is complete, the agitation is stopped and the crystal slurry is allowed to gravity settle for a defined time, and a portion of the supernatant is decanted to reduce the filtration volume. In general, the insulin or insulin analog crystals will have settled within about four or more hours but the actual time may depend on the size of the crystallization vessel.

After crystallization, the entire volume of decanted crystal slurry is then transferred to a filter apparatus. An example of a suitable filter apparatus is an agitated Nutsche filter, which may have a composite sintered stainless steel screen with a pore size that is about 5 μm. The slurry is first gravity filtered, which allows a layer of cake to form on the composite screen with minimal breakthrough. After the target gravity filtrate volume is achieved, the filter apparatus is pressurized to about 0.0138 to 0.034 MPa (about 2 to about 5 psid) or 0.02 MPa (3 psid) or 0.034 MPa (5 psid) with nitrogen to increase filtration flux. Initial filtration is complete when the target filtrate volume is collected, in general, about 89 to 91% or 90% of the crystal slurry filtered. When empty of slurry, the crystallization vessel is rinsed with a defined volume of Cake Wash Solution. The defined volume may be about 4.5% to 5.5% of the initial crystallization volume. The Cake Wash Solution comprises a zinc salt and a crystal stabilizing agent. For example, the Cake Wash Solution may comprise about 66 μM zinc salt, which in particular aspects may be about 8.8 to 9.2 mg/L or 9.0 mg/L zinc chloride and 0.196 to 0.204% (w/v) or 0.2% (w/v) crystal stabilizing agent or meta-cresol.

Following completion of the initial filtration, the vessel rinse is also transferred to the filter apparatus. The filter apparatus is again pressurized to about 0.0138 to 0.034 MPa (about 2 to about 5 psid) or 20 MPa (3 psid) to 0.034 MPa (5 psid) or about 0.027 MPa (4 psid) to remove liquid without allowing the liquid level to drop below the top of the cake bed. The filter cake is then washed a second time with a defined volume of Cake Wash Solution. The defined volume may be about 4.5% to 5.5% of the initial crystallization volume. The filter apparatus is again pressurized to about 0.0138 to 0.034 MPa (about 2 to about 5 psid) or 0.020 MPa (3 psid) to 0.34 MPa (5 psid) or about 0.027 MPa (4 psid) to remove liquid without allowing the liquid level to drop below the top of the cake bed.

Following the second wash, the filter cake is dried using about 0.020 MPa to about 0.048 MPa (about 3 to about 7 psid, respectively) or 0.034 MPa (5 psid) of positive pressure above the cake. Positive pressure is maintained using dry nitrogen, which is regulated at the source. Once no liquid or foam is observed leaving the filter outlet, a vacuum in the range of about −400 to about −380 inches water column (about −747 to −709 mm Hg) or about −400 inches water column (about −747 mmHg or 14.6 psig) may be applied to increase the rate of drying. During drying, the entire cake is agitated with a vertical blade S-impeller, which is lowered into the cake. Drying proceeds until the cake has reached a target moisture content of less than 8%. The final crystallized drug substance is removed from the filter apparatus and packaged and stored until reconstituted.

The present invention therefore further provides a method for preparing insulin or insulin analog crystals which comprises crystallizing the insulin or insulin analog from an aqueous solution comprising the insulin or the insulin analog, a water miscible organic solvent, a crystal stabilizing agent, zinc salt, wherein the solution has a pH greater than the pI of the insulin or insulin analog. The pH is at least 1, 1.5, 2, or 3 pH units greater than the pI of the insulin or insulin analog. In particular aspects, the method may be performed at a temperature at room temperature or within the range of 17° C. to 23° C., or about 20° C., and at a pH within the range of 9.1 to 9.3 pH units, or about 9.2 pH units. In further aspects, the solution is incubated with agitation or stirring. The agitation may be provided by a low shear impeller, for example, an axial flow impeller such as marine impeller or pitched-blade impeller.

In a further aspect of the method, the solution comprises ammonium acetate, which may in particular aspects comprise ammonium acetate at a concentration of about 80 mM to about 150 mM. In a further aspect of the method, the solution comprises ammonium acetate, which may in particular aspects comprise ammonium acetate at a concentration of about 80 mM to about 100 mM. In further aspects, the concentration of the ammonium acetate is about 80 mM to 90 mM. In further aspects, the concentration of the ammonium acetate in the solution is about 85 mM or 85 mM.

In a further aspect of the method, the concentration of the insulin or insulin analog in the solution is about 1 to about 13, 10, 5, 4, or 3 grams of insulin or insulin analog per liter of solution. In a further aspect, the concentration of the insulin or insulin analog in the solution is about 1.75 to about 2.25 grams of insulin or insulin analog per liter of solution. In a particular aspect, the concentration of the insulin or insulin analog in the crystallization solution is about 2 grams per liter.

In a further aspect of the method, the solution may comprise from about 5 to about 20% (v/v) of the water miscible organic solvent. In a further aspect, the solution comprises from about 9% (v/v) to about 11% (v/v) of the water miscible organic solvent. In a further aspect, the solution comprises from about 9.5% (v/v) to about 10.5% (v/v) of the water miscible organic solvent. In a further aspect, the solution comprises about 10% (v/v) of the water miscible organic solvent. In particular aspects, the water miscible organic solvent is isopropanol. The presence of a water miscible solvent is optional.

In particular aspects, the solution comprises from about 0.10% (v/v) to about 0.30% (v/v) of the crystal stabilizing agent. In particular aspects, the solution comprises from about 0.15% (v/v) to about 0.25% (v/v) or 0.2% (v/v) of the crystal stabilizing agent. In a further aspect of the method, the crystal stabilizing agent is a phenolic agent. In a further aspect of the method, the crystal stabilizing agent is selected from the group comprising resorcinol, cresol, meta-cresol, phenol, methyl p-hydroxybenzoate, and methyl 4-hydroxybenzoate. In a particular aspect, the crystal stabilizing agent is meta-cresol.

In a further aspect of the method, the amount of zinc salt in the solution is an amount that provides at least two to four molecules of zinc per molecule of insulin or insulin analog. In particular aspects, the zinc salt is zinc chloride and may be at a concentration of about 13 mg to about 17 mg per gram of insulin or insulin analog. In a particular aspect, the amount of zinc chloride in the solution is 15 mg or about 15 mg per gram of insulin or insulin analog.

In particular aspects of the method, the insulin is native human, porcine, or bovine insulin. In further aspects, the insulin analog is an acid-stable insulin analog, which is stable and soluble in acidic or weakly acidic solutions and insoluble or partially insoluble at physiological pH, or a pI-shifted insulin analog in which the pI of the insulin analog is less than or greater than the pI of native human insulin. The pI of native insulin is 5.4 to 5.6, thus the pI-shifted insulin analog has a pI less than 5.4 or greater than 5.6. In particular aspects, the insulin analog has a pI from between 5.8 to 8.0. An acid-stable insulin analog such as insulin glargine has a pI of about 6.7 to 7.4. In a further aspect, the insulin analog is insulin glargine.

The present invention further provides a method for preparing insulin or insulin analog crystals which comprises: (a) providing a solution comprising the insulin or insulin analog, a water miscible organic solvent, a crystal stabilizing agent, and having a pH at least 1, 1.5, 2, or 3 pH unit greater than the pI of the insulin or insulin analog; and (b) inducing crystallization of the insulin or insulin analog in the solution by adding zinc salt to the solution to provide a crystallization solution that produces the insulin or insulin analog crystals. In particular aspects, the method may be performed at room temperature or a temperature within the range of 17° C. to 23° C., or about 20° C., and at a pH within the range of 9.1 to 9.3 pH units, or about 9.2 pH units. In further aspects, the solution in step (b) is incubated after addition of the zinc salt with agitation or stirring. The agitation may be provided by a low shear impeller, for example, an axial flow impeller such as marine impeller or pitched-blade impeller.

In a further aspect of the method, the solution comprises ammonium acetate, which may in particular aspects comprise ammonium acetate at a concentration of about 80 mM to about 150 mM. In a further aspect of the method, the solution comprises ammonium acetate, which may in particular aspects comprise ammonium acetate at a concentration of about 80 mM to about 100 mM. In further aspects, the concentration of the ammonium acetate is about 80 mM to 90 mM. In further aspects, the concentration of the ammonium acetate in the solution is 85 mM or about 85 mM.

In a further aspect of the method, the concentration of the insulin or insulin analog in the solution is about 1 to 13, 1 to 10, 1 to 5, or 1 to 3 grams of insulin or insulin analog per liter of crystallization solution. In a further aspect, the concentration of the insulin or insulin analog in the solution is about 1.75 to about 2.25 grams of insulin or insulin analog per liter of solution. In a particular aspect, the concentration of the insulin or insulin analog in the crystallization solution is about 2 grams per liter.

In a further aspect of the method, the solution may comprise from about 0% (v/v) to about 20% (v/v) of the water miscible organic solvent. In a further aspect of the method, the solution may comprise from about 5% (v/v) to about 20% (v/v) of the water miscible organic solvent. In a further aspect, the solution comprises from about 9% (v/v) to about 11% (v/v) of the water miscible organic solvent. In a further aspect, the solution comprises from about 9.5% (v/v) to about 10.5% (v/v) of the water miscible organic solvent. In a further aspect, the solution comprises about 10% (v/v) of the water miscible organic solvent. In particular aspects, the water miscible organic solvent is isopropanol.

In particular aspects of the method, the solution comprises from about 0.10% (v/v) to about 0.30% (v/v) of the crystal stabilizing agent. In particular aspects, the solution comprises from about 0.15% (v/v) to about 0.25% (v/v) or 0.2% (v/v) of the crystal stabilizing agent. In a further aspect of the method, the crystal stabilizing agent is a phenolic agent. In a further aspect of the method, the crystal stabilizing agent is selected from the group comprising resorcinol, cresol, meta-cresol, phenol, methyl p-hydroxybenzoate, and methyl 4-hydroxybenzoate. In a particular aspect, the crystal stabilizing agent is meta-cresol.

In a further aspect of the method, the amount of zinc salt in the solution is sufficient to provide about two to four molecules of zinc per six molecules of insulin analog. In particular aspects, the zinc salt is zinc chloride. For example, for zinc chloride, the solution comprises about 13 mg to about 17 mg per gram of insulin or insulin analog. In a particular aspect, the amount of zinc chloride in the solution is 15 mg or about 15 mg per gram of insulin or insulin analog.

In a further aspect of the method, the zinc salt is added to the solution over the course of about 2 to about 5 minutes. In a further aspect of the method, the solution to which the zinc salt has been added is incubated for about 4 or more hours to produce the insulin or insulin analog crystals. In a particular aspect, the solution is incubated for about 4 to about 8 hours to produce the insulin or insulin analog crystals.

In particular aspects, the insulin is native human, porcine, or bovine insulin. In further aspects, the insulin analog is an acid-stable insulin analog, which is stable and soluble in acidic or weakly acidic solutions and insoluble or partially insoluble at physiological pH, or a pI-shifted insulin analog in which the pI of the insulin analog is less than or greater than the pI of native human insulin. The pI of native insulin is 5.4 to 5.6, thus the pI-shifted insulin analog has a pI less than 5.4 or greater than 5.6. In particular aspects the insulin analog has a pI from between 5.8 to 8.0. An acid-stable insulin analog such as insulin glargine has a pI of about 6.7 to 7.4. In a further aspect, the insulin analog is insulin glargine.

The present invention further provides a method for preparing insulin or insulin analog crystals comprising the steps of: (a) providing a solution comprising the insulin or the insulin analog; (b) adding a water miscible organic solvent to the solution of step (a); (c) adjusting the pH of the solution of step (b) to a pH that is at least 1, 1.5, 2, or 3 pH units greater than the pI of the insulin or insulin analog; (d) adding a crystal stabilizing agent to the solution of step (c); (e) adding a zinc salt to the solution in step (d) to provide a crystallization solution and incubating the crystallization solution for a time sufficient for the insulin or insulin analog to crystallize; and (f) collecting the crystallized insulin or insulin analog from the crystallization solution.

In particular aspects, the method may be performed at room temperature or a temperature within the range of 17° C. to 23° C., or about 20° C., and at a pH within the range of 9.1 to 9.3 pH units, or about 9.2 pH units. In a further aspect, after addition of the zinc salt to the solution, the solution is incubated with agitation or stirring. The agitation may be provided by a low shear impeller, for example, an axial flow impeller such as marine impeller or pitched-blade impeller.

In a further aspect of the method, the solution of step (a) comprises ammonium acetate, which may in particular aspects comprise ammonium acetate at a concentration of about 80 mM to about 150 mM. In a further aspect of the method, the solution of step (a) comprises ammonium acetate, which may in particular aspects comprise ammonium acetate at a concentration of about 80 mM to about 100 mM. In further aspects, the concentration of the ammonium acetate is about 80 mM to 90 mM. In further aspects, the concentration of the ammonium acetate in the solution is about 85 mM or 85 mM.

In a further aspect of the method, the concentration of the insulin or insulin analog in the solution is about 1 to 13, 1 to 10, 1 to 5, 1 to 4, or 1 to 3 grams of insulin or insulin analog per liter of crystallization solution. In a further aspect, the concentration of the insulin or insulin analog in the crystallizing solution is about 1.75 to about 2.25 grams of insulin or insulin analog per liter of solution. In a particular aspect, the concentration of the insulin or insulin analog in the crystallization solution is about 2 grams per liter.

In a further aspect of the method, the water miscible organic solvent is added to the solution of step (a) in an amount that provides a solution that comprises about 5% (v/v) to about 20% (v/v) of the water miscible organic solvent. In a further aspect, the water miscible organic solvent that is added provides a solution that comprises about 9% (v/v) to about 11% (v/v) of the water miscible organic solvent. In a further aspect, the water miscible organic solvent that is added provides a solution that comprises about 9.5% (v/v) to about 10.5% (v/v) percent by volume of the water miscible organic solvent. In a further aspect, the water miscible organic solvent that is added provides a solution that comprises about 10% (v/v) percent of the water miscible organic solvent. In particular aspects, the water miscible organic solvent is isopropanol. In particular aspects, the step of adding a water miscible organic solvent is omitted.

In particular aspects of the method, the crystal stabilizing agent is added to the solution of step (c) in an amount that provides a solution that comprises about 0.10% (v/v) to about 0.30% (v/v) of the crystal stabilizing agent. In particular aspects, the crystal stabilizing agent is that is added provides a solution that comprises about 0.15% (v/v) to about 0.25% (v/v) or 0.2% (v/v) of the crystal stabilizing agent. In a further aspect of the method, the crystal stabilizing agent is a phenolic agent. In a further aspect of the method, the crystal stabilizing agent is selected from the group comprising resorcinol, cresol, meta-cresol, phenol, methyl p-hydroxybenzoate, and methyl 4-hydroxybenzoate. In a particular aspect, the crystal stabilizing agent is meta-cresol.

In a further aspect of the method, the amount of zinc salt that is added to the solution is an amount that will provide at least two to four molecules of zinc per six molecules of insulin or insulin analog. In particular aspects the zinc salt is zinc chloride and the zinc chloride is provided in an amount that is about 13 mg to 17 mg per gram of insulin or insulin analog. In a particular aspect, the amount of zinc chloride in the solution is 15 mg or about 15 mg per gram of insulin or insulin analog.

The present invention further provides a method for preparing insulin or insulin analog crystals comprising the steps of: (a) providing a solution comprising the insulin or the insulin analog; (b) adding a water miscible organic solvent to the solution of step (a); (c) adding a crystal stabilizing agent to the solution of step (b); (d) adjusting the pH of the solution of step (c) to a pH that is at least 1, 1.5, 2, or 3 pH units greater than the pI of the insulin or insulin analog; (e) adding a zinc salt to the solution in step (d) to provide a crystallization solution and incubating the crystallization solution for a time sufficient for the insulin or insulin analog to crystallize; and (f) collecting the crystallized insulin or insulin analog from the crystallization solution.

In particular aspects, the method may be performed at room temperature or a temperature within the range of 17° C. to 23° C., or about 20° C., and at a pH within the range of 9.1 to 9.3 pH units, or about 9.2 pH units. In a further aspect, after addition of the zinc salt to the solution, the solution is incubated with agitation or stirring. The agitation may be provided by a low shear impeller, for example, an axial flow impeller such as marine impeller or pitched-blade impeller.

In a further aspect of the method, the solution of step (a) comprises ammonium acetate, which may in particular aspects comprise ammonium acetate at a concentration of about 80 mM to about 150 mM or about 80 mM to about 100 mM. In further aspects, the concentration of the ammonium acetate is about 80 mM to 90 mM. In further aspects, the concentration of the ammonium acetate in the solution is about 85 mM or 85 mM.

In a further aspect of the method, the concentration of the insulin or insulin analog in the solution is about 1 to 13, 1 to 10, 1 to 5, 1 to 4, or 1 to 3 grams of insulin or insulin analog per liter of crystallization solution. In a further aspect, the concentration of the insulin or insulin analog in the crystallizing solution is about 1.75 to about 2.25 grams of insulin or insulin analog per liter of solution. In a particular aspect, the concentration of the insulin or insulin analog in the crystallization solution is about 2 grams per liter.

In a further aspect of the method, the water miscible organic solvent is added to the solution of step (a) in an amount that provides a solution that comprises about 5% (v/v) to about 20% (v/v) of the water miscible organic solvent. In a further aspect, the water miscible organic solvent that is added provides a solution that comprises about 9% (v/v) to about 11% (v/v) of the water miscible organic solvent. In a further aspect, the water miscible organic solvent that is added provides a solution that comprises about 9.5% (v/v) to about 10.5% (v/v) percent by volume of the water miscible organic solvent. In a further aspect, the water miscible organic solvent that is added provides a solution that comprises about 10% (v/v) percent of the water miscible organic solvent. In particular aspects, the water miscible organic solvent is isopropanol. In particular aspects, the step of adding a water miscible organic solvent is omitted.

In particular aspects of the method, the crystal stabilizing agent is added to the solution of step (b) in an amount that provides a solution that comprises about 0.10% (v/v) to about 0.30% (v/v) of the crystal stabilizing agent. In particular aspects, the crystal stabilizing agent is that is added provides a solution that comprises about 0.15% (v/v) to about 0.25% (v/v) or 0.2% (v/v) of the crystal stabilizing agent. In a further aspect of the method, the crystal stabilizing agent is a phenolic agent. In a further aspect of the method, the crystal stabilizing agent is selected from the group comprising resorcinol, cresol, meta-cresol, phenol, methyl p-hydroxybenzoate, and methyl 4-hydroxybenzoate. In a particular aspect, the crystal stabilizing agent is meta-cresol.

In a further aspect of the method, the amount of zinc salt that is added to the solution is an amount that will provide at least two to four molecules of zinc per six molecules of insulin or insulin analog. In particular aspects the zinc salt is zinc chloride and the zinc chloride is provided in an amount that is about 13 mg to 17 mg per gram of insulin or insulin analog. In a particular aspect, the amount of zinc chloride in the solution is 15 mg or about 15 mg per gram of insulin or insulin analog.

In a further aspect of the above embodiments, the zinc salt solution used to induce crystallization of the insulin or insulin analog is added to the solution of step (d) over the course of about 2 to about 5 minutes. In a further aspect of the method, the solution to which the zinc salt has been added is incubated for about 4 or more hours to produce the insulin or insulin analog crystals. In a particular aspect, the solution is incubated for about 4 to about 8 hours to produce the insulin or insulin analog crystals.

In further aspects of the method, the crystallized insulin or insulin analog is collected in a crystal slurry that is amenable to filtration and drying. In a particular aspect, the crystallized insulin or insulin analog is allowed to settle in the crystallization solution by gravity and the supernatant fraction decanted to provide a crystal slurry in a reduced volume that is amenable to filtration and drying.

In particular aspects of the method, the insulin is native human, porcine, or bovine insulin. In further aspects, the insulin analog is an acid-stable insulin analog, which is stable and soluble in acidic or weakly acidic solutions and insoluble or partially insoluble at physiological pH, or a pI-shifted insulin analog in which the pI of the insulin analog is less than or greater than the pI of native human insulin. The pI of native insulin is 5.4 to 5.6, thus the pI-shifted insulin analog has a pI less than 5.4 or greater than 5.6. In particular aspects, the insulin analog has a pI from between 5.8 to 8.0. An acid-stable insulin analog such as insulin glargine has a pI of about 6.7 to 7.4. In a further aspect, the insulin analog is insulin glargine.

The present invention further provides a method for preparing insulin or insulin analog crystals comprising the steps of: (a) providing a first solution comprising the insulin or the insulin analog; (b) adding a water miscible organic solvent to the first solution to provide a second solution comprising about 9% (v/v) to about 11% (v/v) of the water miscible organic solvent; (c) adjusting the pH of the solution to a pH that is at least 1, 1.5, 2, or 3 pH units greater than the pI of the insulin or insulin analog to provide a third solution; (d) adding a crystal stabilizing agent to the third solution to provide a fourth solution; (e) adding zinc salt to the fourth solution to provide a crystallization solution and incubating the crystallization solution for a time sufficient to allow crystallization of the insulin or insulin analog; (f) collecting the crystallized insulin or insulin analog by allowing the crystallized insulin or insulin analog to settle in the crystallization solution and decanting the supernatant from the settled crystallized insulin or insulin analog to produce a crystal slurry; and (g) filtering and drying the decanted crystal slurry to produce the insulin or insulin analog crystals.

In particular aspects, the method may be performed at room temperature or a temperature within the range of 17° C. to 23° C., or about 20° C., and at a pH within the range of 9.1 to 9.3 pH units, or about 9.2 pH units. In a further aspect, after addition of the zinc salt to the third solution, the solution is incubated with agitation or stirring. The agitation may be provided by a low shear impeller, for example, an axial flow impeller such as marine impeller or pitched-blade impeller.

In a further aspect of the method, the first solution comprises ammonium acetate, which may in particular aspects comprise ammonium acetate at a concentration of about 80 mM to about 150 mM or about 80 to about 100 mM. In further aspects, the concentration of the ammonium acetate is about 80 mM to 90 mM. In further aspects, the concentration of the ammonium acetate in the first solution is about 85 mM or 85 mM.

In a further aspect of the method, the amount of the insulin or insulin analog in the first solution is an amount that will provide in the crystallization solution an insulin or insulin analog concentration of about 1 to 13, 1 to 10, 1 to 5, 1 to 4, or 1 to 3 of insulin or insulin analog per liter of crystallization solution. In a further aspect, the concentration of the insulin or insulin analog in the solution is about 1.75 to about 2.25 grams of insulin or insulin analog per liter of solution. In a particular aspect, the concentration of the insulin or insulin analog in the crystallization solution is about 2 grams per liter.

In a further aspect of the method, the water miscible organic solvent is added to the first solution of step (a) in an amount that provides a second solution that comprises about 5% (v/v) to about 20% (v/v) of the water miscible organic solvent. In a further aspect, the water miscible organic solvent that is added provides a second solution that comprises about 9% (v/v) to about 11% (v/v) of the water miscible organic solvent. In a further aspect, the water miscible organic solvent that is added provides a second solution that comprises about 9.5% (v/v) to about 10.5% (v/v) percent by volume of the water miscible organic solvent. In a further aspect, the water miscible organic solvent that is added provides a second solution that comprises about 10% (v/v) percent of the water miscible organic solvent. In particular aspects, the water miscible organic solvent is isopropanol. In particular aspects, the step of adding a water miscible organic solvent is omitted.

In particular aspects of the method the crystal stabilizing agent is added to the third solution of step (c) in an amount that provides a fourth solution that comprises about 0.10% (v/v) to about 0.30% (v/v) of the crystal stabilizing agent. In particular aspects, the crystal stabilizing agent is that is added provides a fourth solution that comprises about 0.15% (v/v) to about 0.25% (v/v) or 0.2% (v/v) of the crystal stabilizing agent. In a further aspect of the method, the crystal stabilizing agent is a phenolic agent. In a further aspect of the method, the crystal stabilizing agent is selected from the group comprising resorcinol, cresol, meta-cresol, phenol, methyl p-hydroxybenzoate, and methyl 4-hydroxybenzoate. In a particular aspect, the crystal stabilizing agent is meta-cresol.

In a further aspect of the method, the amount of zinc salt added to the fourth solution to provide a crystallization solution comprising at least two to four molecules of zinc per six molecules of insulin or insulin analog. In particular aspects the zinc salt is zinc chloride and the zinc chloride is provided in an amount that is about 13 mg to 17 mg per gram of insulin or insulin analog. In a particular aspect, the amount of zinc chloride in the solution is 15 mg or about 15 mg per gram of insulin or insulin analog.

In a further aspect of the method, the zinc salt solution used to induce crystallization of the insulin or insulin analog is added to the fourth solution over the course of about 2 to about 5 minutes. In a further aspect of the method, the solution to which the zinc salt has been added is incubated for about 4 or more hours to produce the insulin or insulin analog crystals. In a particular aspect, the solution is incubated for about 4 to about 8 hours to produce the insulin or insulin analog crystals.

The present invention further provides a method for preparing insulin or insulin analog crystals comprising the steps of: (a) providing a first solution comprising the insulin or the insulin analog; (b) adding a water miscible organic solvent to the first solution to provide a second solution comprising about 9% (v/v) to about 11% (v/v) of the water miscible organic solvent; (c) adding a crystal stabilizing agent to the second solution to provide a third solution; (d) adjusting the pH of the third solution to a pH that is at least 1, 1.5, 2, or 3 pH units greater than the pI of the insulin or insulin analog to provide a fourth solution; (e) adding zinc salt to the fourth solution to provide a crystallization solution and incubating the crystallization solution for a time sufficient to allow crystallization of the insulin or insulin analog; (f) collecting the crystallized insulin or insulin analog by allowing the crystallized insulin or insulin analog to settle in the crystallization solution and decanting the supernatant from the settled crystallized insulin or insulin analog to produce a crystal slurry; and (g) filtering and drying the decanted crystal slurry to produce the insulin or insulin analog crystals.

In particular aspects, the method may be performed at room temperature or a temperature within the range of 17° C. to 23° C., or about 20° C., and at a pH within the range of 9.1 to 9.3 pH units, or about 9.2 pH units. In a further aspect, after addition of the zinc salt to the third solution, the solution is incubated with agitation or stirring. The agitation may be provided by a low shear impeller, for example, an axial flow impeller such as marine impeller or pitched-blade impeller.

In a further aspect of the method, the first solution comprises ammonium acetate, which may in particular aspects comprise ammonium acetate at a concentration of about 80 mM to about 150 mM. In a further aspect of the method, the first solution comprises ammonium acetate, which may in particular aspects comprise ammonium acetate at a concentration of about 80 mM to about 100 mM. In further aspects, the concentration of the ammonium acetate is about 80 mM to 90 mM. In further aspects, the concentration of the ammonium acetate is about 80 mM to 90 mM. In further aspects, the concentration of the ammonium acetate in the first solution is about 85 mM or 85 mM.

In a further aspect of the method, the amount of the insulin or insulin analog in the first solution is an amount that will provide in the crystallization solution an insulin or insulin analog concentration of about 1 to 13, 1 to 10, 1 to 5, 1 to 4, or 1 to 3 of insulin or insulin analog per liter of crystallization solution. In a further aspect, the concentration of the insulin or insulin analog in the solution is about 1.75 to about 2.25 grams of insulin or insulin analog per liter of solution. In a particular aspect, the concentration of the insulin or insulin analog in the crystallization solution is about 2 grams per liter.

In a further aspect of the method, the water miscible organic solvent is added to the first solution of step (a) in an amount that provides a second solution that comprises about 0% (v/v) to about 20% (v/v) of the water miscible organic solvent. In a further aspect of the method, the water miscible organic solvent is added to the first solution of step (a) in an amount that provides a second solution that comprises about 5% (v/v) to about 20% (v/v) of the water miscible organic solvent. In a further aspect, the water miscible organic solvent that is added provides a second solution that comprises about 9% (v/v) to about 11% (v/v) of the water miscible organic solvent. In a further aspect, the water miscible organic solvent that is added provides a second solution that comprises about 9.5% (v/v) to about 10.5% (v/v) percent by volume of the water miscible organic solvent. In a further aspect, the water miscible organic solvent that is added provides a second solution that comprises about 10% (v/v) percent of the water miscible organic solvent. In particular aspects, the water miscible organic solvent is isopropanol. In particular aspects, the step of adding the water miscible organic solvent is omitted.

In particular aspects of the method the crystal stabilizing agent is added to the third solution of step (c) in an amount that provides a third solution that comprises about 0.10% (v/v) to about 0.30% (v/v) of the crystal stabilizing agent. In particular aspects, the crystal stabilizing agent is that is added provides a third solution that comprises about 0.15% (v/v) to about 0.25% (v/v) or 0.2% (v/v) of the crystal stabilizing agent. In a further aspect of the method, the crystal stabilizing agent is a phenolic agent. In a further aspect of the method, the crystal stabilizing agent is selected from the group comprising resorcinol, cresol, meta-cresol, phenol, methyl p-hydroxybenzoate, and methyl 4-hydroxybenzoate. In a particular aspect, the crystal stabilizing agent is meta-cresol.

In a further aspect of the method, the amount of zinc salt added to the fourth solution to provide a crystallization solution comprising at least two to four molecules of zinc per six molecules of insulin or insulin analog. In particular aspects the zinc salt is zinc chloride and the zinc chloride is provided in an amount that is about 13 mg to 17 mg per gram of insulin or insulin analog. In a particular aspect, the amount of zinc chloride in the solution is 15 mg or about 15 mg per gram of insulin or insulin analog.

In a further aspect of the method, the zinc salt solution used to induce crystallization of the insulin or insulin analog is added to the fourth solution over the course of about 2 to about 5 minutes. In a further aspect of the method, the solution to which the zinc salt has been added is incubated for about 4 or more hours to produce the insulin or insulin analog crystals. In a particular aspect, the solution is incubated for about 4 to about 8 hours to produce the insulin or insulin analog crystals.

In further aspects of the above embodiments, the crystallized insulin or insulin analog is collected as a crystal slurry that is amenable to filtration and drying. In particular aspects, the crystallized insulin or insulin analog is allowed to settle in the crystallization solution by gravity and the supernatant fraction decanted to provide a crystal slurry in a reduced volume that is amenable to filtration and drying.

In a further aspect of the method, the crystal slurry is filtered. In a particular aspect, the crystal slurry is filtered using a filter apparatus. In a further aspect, the filter apparatus comprises a composite sintered 5 μm stainless steel screen filter. In a further aspect, the filter apparatus is an agitated Nutsche filter apparatus. In a particular aspect, the decanted slurry is gravity filtered. In a further aspect, the filtration is conducted with a positive overhead pressure in the range of about 0.0138 to 0.034 MPa (about 2 to about 5 psid). In a particular aspect, the filtration is performed with a positive overhead pressure of 0.020 MPa (3 psid) or 0.034 MPa (5 psid) above the cake bed.

In a further aspect of the method, the filter apparatus produces a crystalline insulin or insulin analog cake bed. In a particular aspect of the method, the crystal cake bed is allowed to dry and may be dried at room temperature. In a further aspect, the crystal cake bed is dried in the filter apparatus. In a further aspect, the drying is performed by adding positive overhead pressure above the cake in the range of about 0.020 MPa to about 0.048 MPa (about 3 to about 7 psid, respectively). In a particular aspect, the drying is performed by adding positive overhead pressure of 0.034 MPa (about 5 psid) above the crystal cake bed. In a further aspect of the method, the crystal cake bed is dried by applying vacuum pressure below in the range of about −400 to about −380 inches water column (−747 to −709 mm Hg). In a particular aspect, the crystal cake bed is dried by applying a vacuum pressure of −400 inches water column (−747 mmHg). In a further aspect, the crystal cake bed is dried by simultaneously applying both positive overhead pressure and vacuum pressure below. In a particular aspect of the method, drying of the crystal cake bed proceeds until the moisture content of the cake bed is less than or equal to about 8%.

The present invention further provides a method for preparing insulin or insulin analog crystals comprising the steps of: (a) providing a solution comprising the insulin or the insulin analog; (b) adding a water miscible organic solvent to the solution in step (a) and adjusting the pH of the solution to a pH that is 1, 1.5, 2, or 3 pH units greater than the pI of the insulin or insulin analog; (c) adding a crystal stabilizing agent to the solution of step (b); (d) adding zinc salt to the solution of step (c) to produce a crystallization solution; (e) collecting the crystallized insulin or insulin analog in the crystallization solution to produce a crystal slurry; (f) allowing the crystal slurry to settle in the crystallization solution to produce a settled crystal slurry; (g) decanting the supernatant fraction of the crystallization solution from the settled crystal slurry to produce a decanted crystal slurry; (h) transferring the decanted crystal slurry to a filter apparatus; (i) gravity filtering the decanted crystal slurry; (j) applying positive overhead pressure to the decanted crystal slurry to produce a crystal bed; (k) washing the crystal bed with a wash solution; and (l) drying the crystal bed to produce the insulin or insulin analog crystals.

The present invention further provides a method for preparing insulin or insulin analog crystals comprising the steps of: (a) providing a solution comprising the insulin or the insulin analog; (b) adding a water miscible organic solvent to the solution in step (a); (c) adding a crystal stabilizing agent to the solution of step (b) and adjusting the pH of the solution to a pH that is 1, 1.5, 2, or 3 pH units greater than the pI of the insulin or insulin analog; (d) adding zinc salt to the solution of step (c) to produce a crystallization solution; (e) collecting the crystallized insulin or insulin analog in the crystallization solution to produce a crystal slurry; (f) allowing the crystal slurry to settle in the crystallization solution to produce a settled crystal slurry; (g) decanting the supernatant fraction of the crystallization solution from the settled crystal slurry to produce a decanted crystal slurry; (h) transferring the decanted crystal slurry to a filter apparatus; (i) gravity filtering the decanted crystal slurry; (j) applying positive overhead pressure to the decanted crystal slurry to produce a crystal bed; (k) washing the crystal bed with a wash solution; and (l) drying the crystal bed to produce the insulin or insulin analog crystals.

In particular aspects of the above embodiments, the method may be performed at room temperature or a temperature within the range of 17° C. to 23° C., or about 20° C., and at a pH within the range of 9.1 to 9.3 pH units, or about 9.2 pH units. In a further aspect, after addition of the zinc salt to the solution, the solution is incubated with agitation or stirring. The agitation may be provided by a low shear impeller, for example, an axial flow impeller such as marine impeller or pitched-blade impeller.

In a further aspect of the above embodiments, the solution in step (a) comprises ammonium acetate, which may in particular aspects comprise ammonium acetate at a concentration of about 80 mM to about 150 mM. In a further aspect the ammonium acetate is at a concentration of about 80 mM to about 100 mM. In further aspects, the concentration of the ammonium acetate is about 80 mM to 90 mM. In further aspects, the concentration of the ammonium acetate in the first solution is about 85 mM or 85 mM.

In further aspects, the solution has a starting pH of about 2.9 to about 3.1. In a particular aspect, the starting pH is 3.0.

In a further aspect of the method, the concentration of the insulin or insulin analog in the solution is about is about 1 to 13, 1 to 10, 1 to 5, 1 to 4, or 1 to 3 of insulin or insulin analog per liter of crystallization solution. In a further aspect, the concentration of the insulin or insulin analog in the solution is about 1.75 to about 2.25 grams of insulin or insulin analog per liter of solution. In a particular aspect, the concentration of the insulin or insulin analog in the crystallization solution is about 2 grams per liter.

In a further aspect of the method, the water miscible organic solvent is added to the solution of step (a) in an amount that provides a solution that comprises about 0% (v/v) to about 20% (v/v) of the water miscible organic solvent. In a further aspect, the water miscible organic solvent is added to the solution of step (a) in an amount that provides a solution that comprises about 5% (v/v) to about 20% (v/v) of the water miscible organic solvent. In a further aspect, the water miscible organic solvent that is added provides a solution that comprises about 9% (v/v) to about 11% (v/v) of the water miscible organic solvent. In a further aspect, the water miscible organic solvent that is added provides a solution that comprises about 9.5% (v/v) to about 10.5% (v/v) percent by volume of the water miscible organic solvent. In a further aspect, the water miscible organic solvent that is added provides a solution that comprises about 10% (v/v) percent of the water miscible organic solvent. In particular aspects, the water miscible organic solvent is isopropanol. In particular aspects, the step of adding the water miscible organic solvent is omitted.

In particular aspects of the method, the crystal stabilizing agent is added to the solution of step (b) in an amount that provides a solution that comprises about 0.10% (v/v) to about 0.30% (v/v) of the crystal stabilizing agent. In particular aspects, the crystal stabilizing agent is that is added provides a solution that comprises about 0.15% (v/v) to about 0.25% (v/v) or 0.2% (v/v) of the crystal stabilizing agent. In a further aspect of the method, the crystal stabilizing agent is a phenolic agent. In a further aspect of the method, the crystal stabilizing agent is selected from the group comprising resorcinol, cresol, meta-cresol, phenol, methyl p-hydroxybenzoate, and methyl 4-hydroxybenzoate. In a particular aspect, the crystal stabilizing agent is meta-cresol.

In a further aspect of the method, the amount of zinc salt that is added to the solution of step (c) is an amount that will provide at least two to four molecules of zinc per six molecules of insulin or insulin analog. In particular aspects the zinc salt is zinc chloride and the zinc chloride is provided in an amount that is about 13 mg to 17 mg per gram of insulin or insulin analog. In a particular aspect, the amount of zinc chloride in the solution is 15 mg or about 15 mg per gram of insulin or insulin analog. In a further aspect of the method, the zinc salt is added to the solution over the course of about 2 to about 5 minutes.

In a further aspect of the method, the crystallization reaction time is greater than or equal to 4 hours. In a particular aspect, the crystallization reaction time is in the range of about 4 to about 8 hours.

In further aspects, the crystallized insulin or insulin analog is collected as a crystal slurry amenable to filtration and drying. In a further aspect, the slurry can be allowed to settle by gravity and decanted to provide a decanted crystal slurry in a reduced volume amendable to filtration and drying.

In a further aspect of the method, the decanted crystal slurry is filtered. In a particular aspect, the filtration is conducted in a filter apparatus. In a further aspect, the filter is a composite sintered 5 μm stainless steel screen. In a further aspect, the filter apparatus is an agitated Nutsche filter.

In a particular aspect, the filter volume endpoint is in the range of about 85 to about 90 percent of the crystal slurry. In a particular aspect, the filtrate volume endpoint is 90 percent of the crystal slurry.

In a particular aspect, the decanted crystal slurry is gravity filtered. In a further aspect, the filtration is conducted with a positive overhead pressure in the range of about 0.0138 to 0.034 MPa (about 2 to about 5 psid). In a particular aspect, the filtration is performed with a positive overhead pressure of 0.020 MPa (3 psid) or 0.034 MPa (5 psid) above the crystal cake bed.

In a particular aspect of the method, the filtration produces a crystalline insulin or insulin analog cake bed.

In a further aspect of the method, the crystal cake bed is washed with a wash solution comprising a zinc salt and a crystal stabilizing agent. For example, the wash solution may comprise about 8.8 to 9.2 mg/L or 9.0 mg/L zinc salt and 0.196 to 0.204% (w/v) or 0.2% (w/v) crystal stabilizing agent. In further aspects, the crystal stabilizing agent is selected from the group comprising resorcinol, cresol, meta-cresol, phenol, methyl p-hydroxybenzoate, and methyl 4-hydroxybenzoate. In a further aspect, the crystal stabilizing agent is meta-cresol. The zinc salt may be zinc chloride.

In a particular aspect of the method, the volume of wash solution used to wash the crystal cake bed is in the range of at least 4 times the volume of the initial crystallization solution. In a particular aspect, the volume of wash solution to wash the cake bed is 5 times the volume of the initial crystallization solution. In further aspects, the crystal cake bed may be washed multiple times.

In a further aspect of the method, the filtration may be conducted with agitation, which may in particular aspects, be conducted at a speed of about 90 to about 110 centimeters per second. In a particular aspect, the filtration is agitated at a speed of 100 centimeters per second. The agitation may be provided by a low shear impeller, for example, an axial flow impeller such as marine impeller or pitched-blade impeller.

In a particular aspect of the method, the crystal cake bed is allowed to dry. In a further aspect, the crystal cake bed is dried in the filter apparatus. In a further aspect, the drying is performed by adding positive overhead pressure above the crystal cake bed in the range of about 0.020 MPa to about 0.048 MPa (about 3 to about 7 psid, respectively). In a particular aspect, the drying is performed by adding positive overhead pressure of 0.034 MPa (about 5 psid) above the crystal cake bed. In a further aspect of the method, the crystal cake bed is dried by applying vacuum pressure in the range of about −400 to about −380 inches water column (−747 to −709 mm Hg). In a particular aspect, the crystal cake bed is dried by applying a vacuum pressure of −400 inches water column (−747 mmHg). In a further aspect, the crystal cake bed is dried by both positive overhead pressure and vacuum pressure below. In a particular aspect of the method, drying of the crystal cake bed proceeds until the effluent relative humidity has reached a moisture content of less than or equal to 8%.

In a further aspect of the method, the drying may be conducted with agitation, which may be provided by a low shear impeller, for example, an axial flow impeller such as marine impeller or pitched-blade impeller. In a particular aspect, the crystal cake bed may be agitated during drying using a vertical blade impeller. In a further aspect, the crystal cake bed may be agitated during drying using a vertical blade impeller which is lowered into the cake at a drop rate of about 2 to about 3 millimeters every 15 minutes.

The present invention further provides a method for preparing insulin glargine crystals comprising (a) providing a solution comprising the insulin glargine, a water miscible organic solvent, and a crystal stabilizing agent, wherein the solution has a pH that is at least 1, 1.5, 2, or 3 pH units greater than the pI of the insulin glargine, and (b) adding a zinc salt to the solution to provide a crystallization solution and incubating the crystallization solution for a time sufficient for the insulin glargine to crystalize produce the insulin glargine crystals.

In particular aspects of the method the incubation is performed at room temperature or a temperature of about 17° C. to 23° C. In further aspects of the method, the time sufficient to produce the insulin glargine crystals is about 4 to 8 hours incubation. In further aspects, the solution in step (b) is incubated with agitation or stirring. The agitation may be provided by a low shear impeller, for example, an axial flow impeller such as marine impeller or pitched-blade impeller. In particular aspects, the impeller has a pitch of 10° or less from the vertical. In a further aspect, the solution is agitated with an impeller tip speed from about 45 to 55 cm/s, which in particular aspects may be 50 cm/s.

In particular aspects of the method, the insulin glargine is at a concentration of about 1 to 13, 1 to 10, 1 to 5, 1 to 4, or 1 to 3 of insulin or insulin analog per liter of crystallization solution. In a further aspect, the insulin glargine is at a concentration in the range of 1.75 g/L of 2.25 g/L or is at a concentration of about 2.0 g/L.

In particular aspects of the method the crystallization solution comprises ammonium acetate, which may be a concentration of about 80 to 150 mM. In particular aspects of the method the crystallization solution comprises ammonium acetate, which may be a concentration of about 80 to 100 mM or about 80 to 90 mM. In further aspects, the concentration of the ammonium acetate in the first solution is about 85 mM or 85 mM. In particular aspects of the method, the water miscible organic solvent is present in the crystallization solution in an amount that corresponds to about 9.5% (v/v) to 10.5% (v/v) of the solution or about 10% (v/v) of the solution. In further aspects of the method, the water miscible organic solvent is selected from the group consisting of ethanol, methanol, acetone, and isopropanol. In a further aspect of the method, the water miscible organic solvent is isopropanol. In particular aspects, the water miscible organic solvent is omitted.

In particular aspects, the crystal stabilizing agent is a phenolic agent selected from the group comprising resorcinol, cresol, meta-cresol, phenol, methyl p-hydroxybenzoate, and methyl 4-hydroxybenzoate. In further aspects, the crystal stabilizing agent is meta-cresol. The crystal stabilizing agent may be at a concentration of about 0.15% (v/v) to 0.25% (v/v) or about 0.20% (v/v).

The pH of the solution in step (a) is adjusted to provide a solution wherein the pH of the solution is from about 9.1 to 9.3 pH units or about 9.2 pH units. The pH may be adjusted after adding the water miscible organic solvent to the solution or after the crystal stabilizing agent has been added to the solution provided that the pH is adjusted to from about 9.1 to 9.3 pH units or about 9.2 pH units prior to addition of the zinc salt to the solution.

In particular aspects of the method, the amount of zinc salt that is added is an amount sufficient to provide at least two to four molecules of zinc per six molecules of insulin glargine. In a further aspect of the method, the zinc salt is zinc chloride. When the zinc salt is zinc chloride, the zinc chloride is added to provide a final concentration of about 13.2 mg to 16.8 mg zinc salt per gram insulin glargine.

In further aspects of the method, a crystal slurry comprising the insulin glargine crystals is produced following addition of the zinc salt to the solution by allowing the insulin glargine crystals in the solution to settle in the solution by gravity and the solution decanted from the settled insulin glargine crystals to produce a decanted crystal slurry. In particular aspects, the insulin glargine crystals are allowed to settle for about five hours or more prior to decanting the solution to produce a decanted crystal slurry.

In a further aspect, the decanted crystal slurry is applied to a filter apparatus to remove the solution from the crystal slurry to produce a crystal cake and drying the crystal cake on the filter apparatus to provide the crystal insulin glargine. In a particular aspect, the decanted crystal slurry is gravity filtered to produce the crystal cake bed. In a further aspect, the filtration is conducted with a positive overhead pressure in the range of about 0.0138 to 0.034 MPa (about 2 to about 5 psid) to produce the crystal cake bed, which is dried in the filter apparatus. In a particular aspect, the filtration is performed with a positive overhead pressure of 0.020 MPa (3 psid) or 0.034 (5 psid) above the crystal cake bed and the crystal cake bed dried in the filter apparatus. In a further aspect, the filter apparatus is an agitated Nutsche filter.

In general the method disclosed herein will produce insulin or insulin analog crystals that have an average diameter equal to or greater than 10 µm. These crystals are amendable to drying on a filter with a pore size of about 5 µm. Adjusting the parameters of the method disclosed herein may produce crystals that have an average diameter less than 10 µm. These smaller crystals may be dried on filters having a pore size less than 5 µm. Thus, the present invention further provides a method for producing crystals of insulin or insulin analog wherein the insulin or insulin analog crystals are separated from the crystallizing solution by gravity and decanting the crystallizing solution to provide a crystal slurry, which is applied to the filter or screen in a filter apparatus such as a Nutsche filter apparatus to remove any remaining crystallizing solution to produce a crystal cake that is dried on the same apparatus wherein the pore size of the filter or screen in the filter apparatus is sufficient to prevent passage of the crystals without clogging filter.

The following examples are intended to promote a further understanding of the present invention.

EXAMPLE 1

Figure 1B:
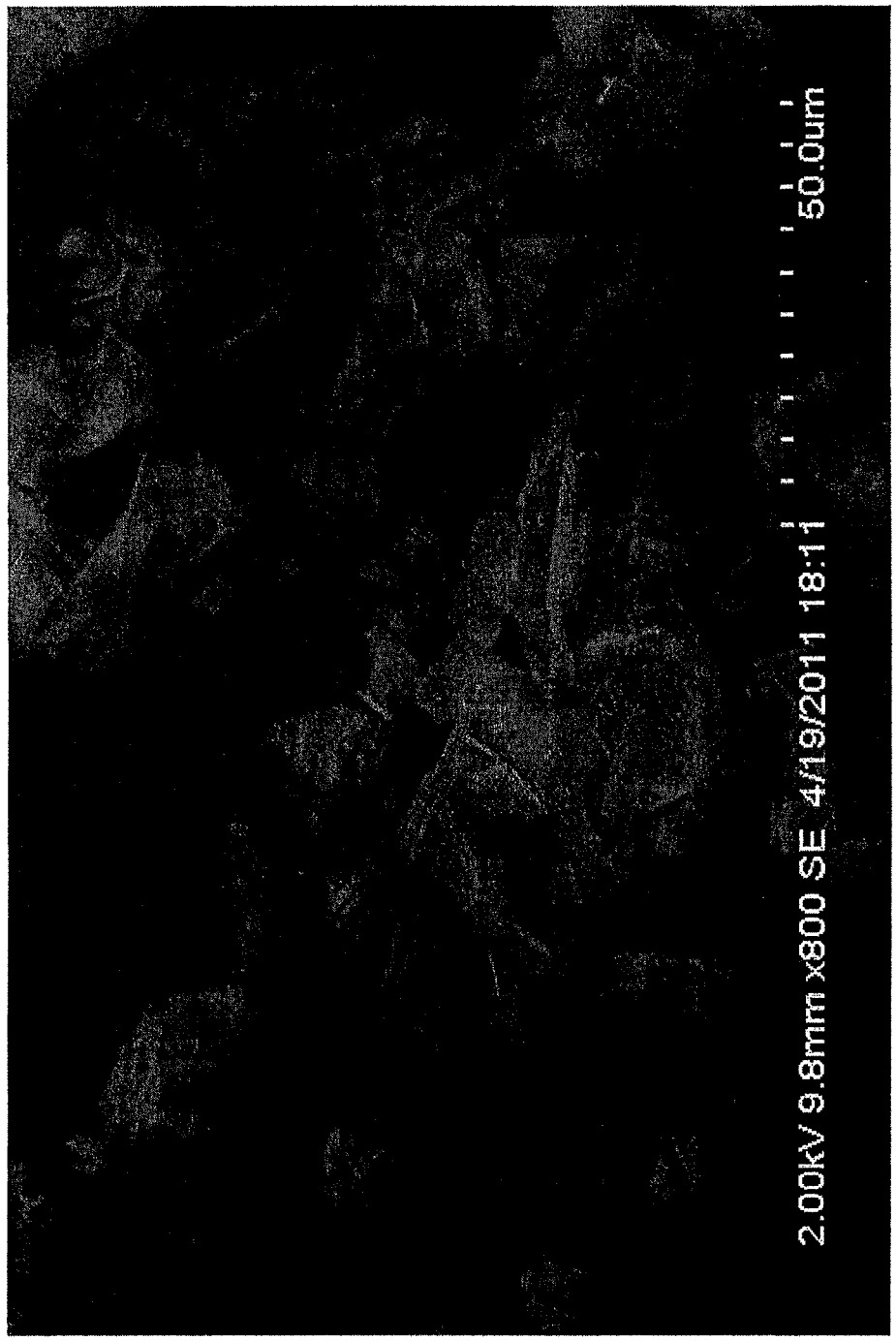
FIG. 1B shows a scanning electron microscope image of insulin glargine crystals produced by the method disclosed herein.

In a vessel comprising a low shear, marine impeller positioned at a pitch from the vertical of 10 degrees or less, a concentrated solution of insulin glargine in 100 mM ammonium acetate, pH 3.1 buffer is diluted with 100 mM ammonium acetate, pH 3.1 buffer to provide a diluted solution in which the final concentration of the insulin glargine is such that when isopropanol, meta-cresol, and zinc chloride solution are added to the solution in the correct ratios and the pH adjusted to provide the crystallization solution, the final concentration of the insulin glargine in the crystallization solution is about 2.0 g/L. Isopropanol is added to the diluted solution to provide a final concentration of about 10% (v/v) isopropanol and the pH of the solution adjusted to about 9.2±0.1 pH units with ammonium hydroxide. Then meta-cresol is added to the solution to provide a concentration of about 0.20% (w/v) with agitation (about 100 cm/s) in order to ensure its dispersion. In order to induce crystallization, a 3% (w/v) zinc chloride solution is added to the solution at a ratio of 0.50 mL of zinc chloride solution per gram insulin glargine and the mixture is allowed to form crystals at room temperature with mild agitation (about 50 cm/s) for 4 to 8 hours. As shown in FIG. 1A and FIG. 1B, the crystals that form following the method herein are substantially homogeneous in size and have an average size that is greater than 10 μm.

Following crystallization, the crystals in the mixture are allowed to settle for five or more hours, the time depending on the volume of the mixture in the vessel. At the end of this settling period, decanting is performed by pumping liquid from the top of the vessel to a secondary vessel or to waste leaving behind a decanted crystal slurry. The amount of mother liquor removed will be dependent on the height of the agitator as well as the means used to siphon off the material. By removing the liquid above the settled crystals, the amount of slurry material filtered is reduced as are any fines, which may be created during the crystallization or as a result of agitation. In order to resuspend the crystals in the decanted crystal slurry, agitation at about 50 cm/s is resumed.

The entire volume of decanted crystal slurry is transferred to an agitated Nutsche filter, which includes a composite sintered stainless steel screen (BOPP Poremet SS316 Composite Media, 5 μm pore size) and a movable and adjustable vertical S-impeller for agitation. Filtration of the crystals is performed in two steps. In the first step, the slurry is gravity filtered, i.e. without applying overhead pressure, which allows a layer of cake to form on the screen with little to no breakthrough. Gravity filtration is allowed to continue until a calculated target filtrate volume, representing 400 g/m$^2$ crystal bed formation on the screen, is collected. In the second step, 0.013 to 0.027 MPa (2-4 psid) of overhead pressure is applied to the filter to increase filtration flux. In order to prevent the crystal bed from drying, filtration is continued until about 90% of the post-decant crystal slurry weight is collected as filtrate.

When empty of crystal slurry, the crystallization vessel is rinsed through a sprayball with a volume of Cake Wash Solution (9 mg/mL zinc chloride, 0.2% (w/v) meta-cresol) equivalent to 5% of the initial pre-decant crystal slurry weight. This wash is transferred to the filter, and overhead pressure of about 0.020 MPa (3 psid) is applied to the filter until about 90% of the post-decant crystal slurry weight is collected as filtrate.

Next, the cake is washed a second time with a defined volume of Cake Wash Solution, injected directly into the filter, also through a sprayball. The second wash is complete when all liquid is removed from the filter apparatus and foam is observed to come through the filter apparatus outlet.

Following the second wash, the cake is dried at room temperature using positive pressure at about 0.034 MPa (5 psid) above the cake and pulling a vacuum of about −747 mm Hg (−400 inches of water column) from below the cake. Positive pressure is maintained using dry nitrogen, which is regulated at the source. Drying proceeds until effluent humidity has reached the specified criteria at which point agitation is initiated. During drying, the entire cake is agitated with a vertical blade S-impeller, which is lowered into the cake at a specified drop rate of about 2-3 mm per15 minutes and a rotational speed rate of about 35 rpm. The final crystallized drug substance is swept from the filter apparatus and stored with humidity control until reconstitution.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A method for preparing insulin glargine crystals comprising:
   (a) providing a solution comprising the insulin glargine, a water miscible organic solvent, and a crystal stabilizing agent, wherein the solution has a pH that is at least 1 pH unit greater than the pI of the insulin glargine; and
   (b) adding a zinc salt to the solution and incubating the solution for a time sufficient for the insulin glargine to crystallize and produce the insulin glargine crystals.

2. The method in claim 1, wherein the solution comprises ammonium acetate.

3. The method in claim 1, wherein the insulin glargine is at a concentration in the range of 1.75 g/L to 2.25 g/L.

4. The method in claim 1, wherein the water miscible organic solvent is selected from the group consisting of ethanol, methanol, acetone, and isopropanol.

5. The method in claim 1, wherein the water miscible organic solvent is isopropanol.

6. The method in claim 1, wherein the water miscible organic solvent is present in an amount which corresponds to about 9.5% (v/v) to 10.5% (v/v) of the solution.

7. The method in claim 1, wherein the crystal stabilizing agent is a phenolic agent selected from the group consisting of resorcinol, cresol, meta-cresol, phenol, methyl p-hydroxybenzoate, and methyl 4-hydroxybenzoate.

8. The method in claim 1, wherein the crystal stabilizing agent is meta-cresol.

9. The method in claim 1, wherein the zinc salt is zinc chloride.

10. The method in claim 1, wherein the amount of zinc salt added to the solution is sufficient to provide at least two molecules of zinc per six molecules of insulin glargine.

11. The method of claim 1, wherein the pH of the solution is from about 9.1 to 9.3.

12. The method of claim 1, wherein the pH of the solution is about 9.2.

13. The method of claim 1, wherein the crystallization is performed at a temperature of about 17° C. to 23° C.

14. The method in claim 1, wherein a crystal slurry comprising the insulin glargine crystals is produced by allowing the insulin glargine crystals in the solution to settle in the solution and the solution is decanted from the settled insulin glargine crystals to produce a decanted crystal slurry.

15. The method in claim 14, wherein the insulin glargine crystals are allowed to settle for about five hours or more prior to decanting the solution to produce the decanted crystal slurry.

16. The method of claim 14, wherein the decanted crystal slurry is applied to a filter apparatus to remove the solution from the decanted crystal slurry to produce a crystal cake bed and drying the crystal cake bed to provide the insulin glargine crystals.

17. The method of claim 16, wherein the crystal cake bed is dried in the filter apparatus.

18. The method of claim 16, wherein the filter apparatus is a Nutsche filter.

19. The method of claim 1, wherein the insulin glargine crystals are 10 μm or greater in size.

* * * * *

SEQUENCE LISTING

```
<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```